United States Patent
Grandy

(10) Patent No.: US 11,185,681 B2
(45) Date of Patent: Nov. 30, 2021

(54) DEVICE FOR MANAGING THE OPERATION OF AN ARTIFICIAL HEART

(71) Applicant: AVANTIX, Aix-en-Provence (FR)

(72) Inventor: Patrick Grandy, Rognac (FR)

(73) Assignee: AVANTIX, Aix-en Provence (FR)

( * ) Notice: Subject to any disclaimer, the term of this patent is extended or adjusted under 35 U.S.C. 154(b) by 245 days.

(21) Appl. No.: 15/517,364

(22) PCT Filed: Oct. 9, 2015

(86) PCT No.: PCT/EP2015/073481
§ 371 (c)(1),
(2) Date: Jul. 17, 2017

(87) PCT Pub. No.: WO2016/055652
PCT Pub. Date: Apr. 14, 2016

(65) Prior Publication Data
US 2017/0312072 A1    Nov. 2, 2017

(30) Foreign Application Priority Data

Oct. 10, 2014   (FR) ..................... 1459759

(51) Int. Cl.
*A61M 60/50* (2021.01)
*A61M 60/871* (2021.01)
(Continued)

(52) U.S. Cl.
CPC .......... *A61M 60/50* (2021.01); *A61M 60/871* (2021.01); *A61F 2/482* (2021.08);
(Continued)

(58) Field of Classification Search
CPC ...... A61M 1/1086; A61M 1/127; A61M 1/12; A61M 2205/04; A61M 2205/8206; A61F 2/24; A61F 2002/482; A61F 2250/0001
See application file for complete search history.

(56) References Cited

U.S. PATENT DOCUMENTS

| | | | |
|---|---|---|---|
| 5,941,906 A * | 8/1999 | Barreras, Sr. ...... | A61N 1/36071 607/66 |
| 6,183,412 B1 * | 2/2001 | Benkowski ......... | A61M 1/1031 600/16 |

(Continued)

FOREIGN PATENT DOCUMENTS

| EP | 2 255 839 A1 | 12/2010 |
|---|---|---|
| WO | WO 2012/012552 A1 | 1/2012 |
| WO | WO 2013/173643 A1 | 11/2013 |

OTHER PUBLICATIONS

International Search Report as issued in International Patent Application No. PCT/EP2015/073481, dated Mar. 8, 2016.

*Primary Examiner* — Lynsey C Eiseman
*Assistant Examiner* — Jessandra F Hough
(74) *Attorney, Agent, or Firm* — Arc IP Law, PC; Joseph J. Mayo

(57) ABSTRACT

A device for controlling the functioning of a cardiac prosthesis, the device for controlling includes a control path, the control path having a control system designed and arranged to monitor and regulate the electrical supply of a cardiac prosthesis; a first insulating system designed and arranged to electrically insulate the cardiac prosthesis from the electrical supply; and a controller designed and arranged to monitor and regulate the electrical supply.

6 Claims, 3 Drawing Sheets

(51) Int. Cl.
*A61M 60/122* (2021.01)
*A61F 2/48* (2006.01)

(52) U.S. Cl.
CPC .... *A61F 2250/0001* (2013.01); *A61M 60/122* (2021.01); *A61M 2205/04* (2013.01); *A61M 2205/8206* (2013.01)

(56) References Cited

U.S. PATENT DOCUMENTS

| | | | | |
|---|---|---|---|---|
| 2004/0255195 | A1* | 12/2004 | Larson | G06F 11/221 714/30 |
| 2006/0252977 | A1* | 11/2006 | Sullivan | A61M 1/10 600/16 |
| 2008/0221495 | A1* | 9/2008 | Steffens | A61M 1/10 604/4.01 |
| 2012/0035418 | A1* | 2/2012 | Talbert | A61B 1/00016 600/109 |
| 2013/0289334 | A1* | 10/2013 | Badstibner | A61M 1/127 600/16 |
| 2015/0066142 | A1* | 3/2015 | Smith | A61M 60/857 623/3.13 |
| 2016/0022891 | A1* | 1/2016 | Bluvshtein | A61M 1/127 600/16 |
| 2018/0339093 | A1* | 11/2018 | Zilbershlag | H01M 50/172 |

* cited by examiner

DEVICE FOR MANAGING THE OPERATION OF AN ARTIFICIAL HEART

CROSS-REFERENCE TO RELATED APPLICATIONS

This is the U.S. National Stage of PCT/EP2015/073481, filed Oct. 9, 2015, which in turn claims priority to French Application No. 1459759, filed Oct. 10, 2014, the entire contents of all applications are incorporated herein by reference in their entireties.

TECHNICAL FIELD

The present invention relates to a device for managing the operation of an artificial heart. More specifically, the device for managing the operation of an artificial heart according to the invention seeks to supervise and control the electrical power of an artificial heart. It also seeks to supervise the operation of the artificial heart so as to be able to affect the prosthesis or create a warning when it malfunctions.

STATE OF THE PRIOR ART

Habitually, when a person suffers from a substantial cardiac deficiency a heart transplant may be the only conceivable cure. In this case the deficient heart is replaced by a healthy heart taken from a donor. Bearing in mind the small number of donors, an implantable and independent artificial heart which attempts to reproduce faithfully the operation of the natural heart has been developed. The electrical energy required for the operation of the artificial heart can be provided in two different ways.

A first way consists in supplying the electrical energy required to operate the artificial heart by means of a portable battery which the patient can wear on them. The artificial heart is then connected to the portable battery by means of a wire passing through a cutaneous micro-perforation. By this means the external portable battery supplies the electrical power for the electronics of the artificial heart over this wire.

A second way consists in supplying the electrical energy required to operate the artificial heart by means of a hospital console. This type of power is generally used during the post-operative period.

Each power supply is controlled by a separate device operating independently. More specifically, the portable energy supply is controlled by a portable control device, while the power supplied by the hospital console is controlled by the hospital console. These two power management devices are obviously impractical and expensive.

DESCRIPTION OF THE INVENTION

One goal of the invention is therefore to remedy the disadvantages of the state of the art. Against this background, the purpose of the present invention is to provide a device for managing the operation of an artificial heart which is safe for the person fitted with such an artificial heart, and inexpensive.

To this end the invention relates to a device for managing the operation of an artificial heart, where the device for managing the operation of an artificial heart includes a management channel, and where the management channel includes:

management means manufactured and arranged to supervise and control the electrical power supply of an artificial heart, first insulation means manufactured and arranged to insulate the artificial heart electrically from the electrical power supply, and management means manufactured and arranged to supervise and control the electrical power supply.

By virtue of the invention a single device is able to supervise and control the electrical power supply of an artificial heart. The device according to the invention is also fitted with first means to insulate the artificial heart electrically from the electrical power supply, enabling safe operation of the artificial heart, and consequently the safety of the wearer of the artificial heart.

The device for managing the operation of an artificial heart according to the invention may also have one or more of the characteristics below, considered individually, or in all technically possible combinations:

In a non-restrictive implementation, the electrical power supply is provided by a portable electrical power supply and/or a fixed electrical power supply.

In a non-restrictive implementation, the first insulation means are manufactured and arranged to insulate the artificial heart electrically from the fixed electrical power supply.

In a non-restrictive implementation, the first insulation means are manufactured and arranged to insulate the artificial heart electrically from the portable electrical power supply.

In a non-restrictive implementation, the first insulation means are in compliance with standard NF-EN 60601-1.

In a non-restrictive implementation, the management channel also includes an interface for communicating with the artificial heart, where the communication interface is formed by an interface of the CAN or RS232 type.

In a non-restrictive implementation, the management channel also includes a communication isolator installed between the management means and the communication interface.

In a non-restrictive implementation, the management channel includes measuring means manufactured and arranged to measure the atmospheric pressure.

In a non-restrictive implementation, the management channel includes warning means manufactured and arranged to communicate with the management means so as to warn a user when an operational fault of the electrical power supply, of the management channel, of a second management channel and/or of the artificial heart is detected by the management means.

In a non-restrictive implementation, the management channel includes at least one external interface manufactured and arranged to allow communications between the management means and an external device.

In a non-restrictive implementation, the device for managing the operation of an artificial heart also includes a second management channel, where the second management channel is identical to the first management channel according to the invention.

In a non-restrictive implementation, the first management channel and the second management channel are installed in parallel, where the device for managing operation also includes second means for insulating the first management channel and the second management channel.

BRIEF DESCRIPTION OF THE FIGURES

Other characteristics and advantages of the invention will become clear from the description which is given of it below, by way of example and non-restrictively, with reference to the appended figures, in which.

For reasons of clarity only elements of use in understanding the invention have been represented, not to scale, and schematically. In addition, similar elements in different figures have identical references.

DETAILED DESCRIPTION OF AT LEAST ONE IMPLEMENTATION OF THE INVENTION

Figure 1:
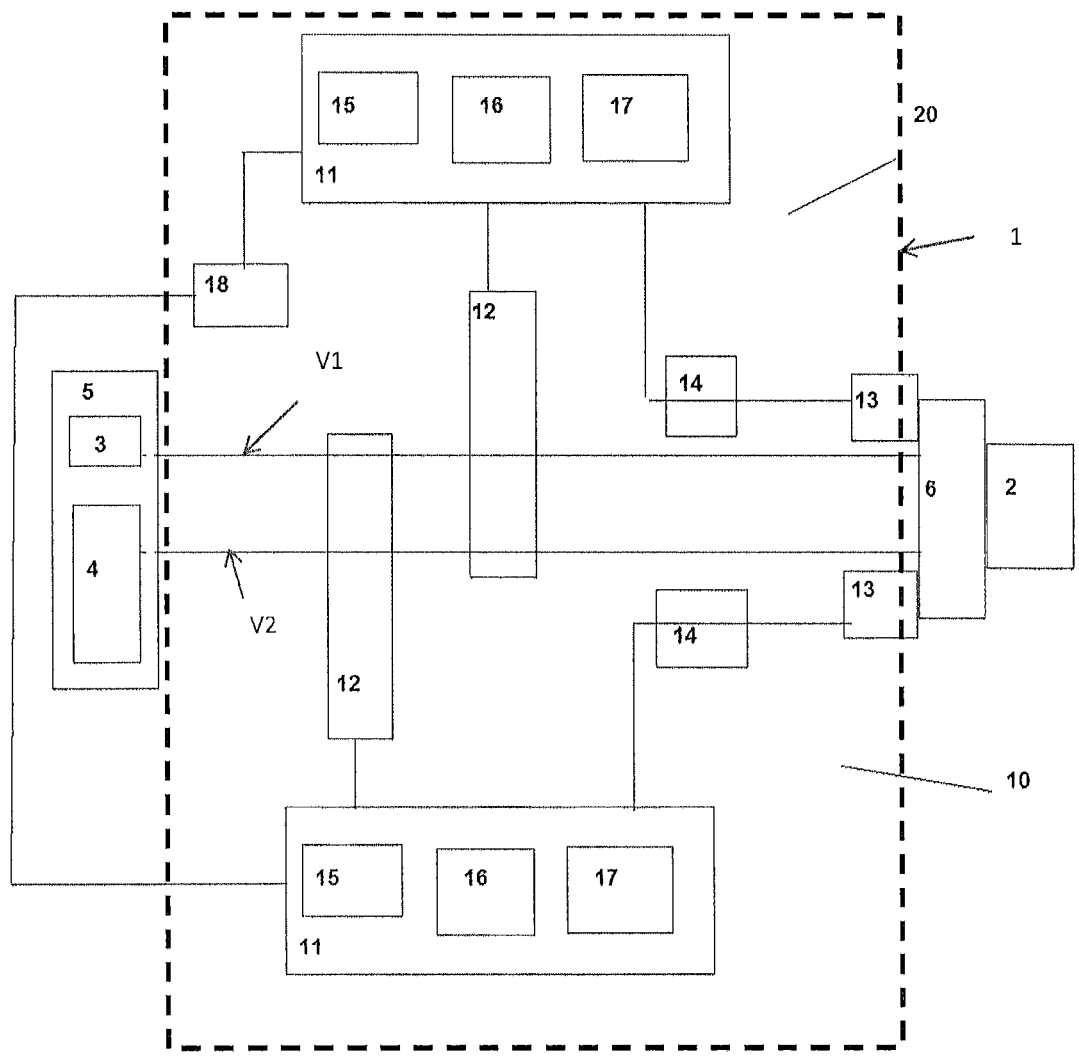
FIG. 1 illustrates, diagrammatically, a first example implementation of a device for managing the operation of an artificial heart in accordance with the invention.

FIG. 1 illustrates an example embodiment of a device 1 for managing the operation of an artificial heart 2 in accordance with the invention.

More specifically, an artificial heart 2 of this type has an unrepresented internal device. Such an internal device consists of sensors located on artificial heart 2 connected to a microprocessor located under the case of artificial heart 2. To provide cardiac function regulation meeting the variable requirements of the person wearing this prosthesis the sensors record arterial pressure data and position data (rest periods and physical efforts). The microprocessor receives this data and continuously processes it. It is a genuine embedded computer, which ensures that the cardiac rhythm is suitable for the body's requirement, in particular by operating motorised pumps included in prosthesis 2 more or less rapidly.

Device 1 for managing operation of artificial heart 2 according to the invention is formed by a unit which may be fixed or worn on the patient. Management device 1 supplies information to the patient and relays remote diagnosis data to the hospital in order to monitor the wearer of artificial heart 2 remotely. This 24 h-a-day monitoring service allows the internal data relating to artificial heart 2 and the patient's physiological data to be monitored.

In general terms, to guarantee the patient's safety, management device 1 has two electrical power channels V1 and V2 which are fully independent from one another, in the event that one of them is defective.

When management device 1 is fixed (in other words connected to a hospital console) or portable and is operating in a manner called "independent operation", two power supplies 5 can be used, namely a battery of hospital console 4 and a portable battery 3. By this means the electrical energy required to operate artificial heart 2 is provided by a portable battery 3 and/or by a battery of hospital console 4. Artificial heart 2 is connected to portable battery 3, to hospital console 4 and to management device 1 via a connection interface 6 which is accessible through a cutaneous micro-perforation of the wearer of artificial heart 2. This connection interface 6 consequently enables electrical power supply 5 to be connected, and also management device 1, which conveys the data between the electronics embedded in artificial heart 2 and itself, in order to supervise and manage artificial heart 2.

Figure 2:
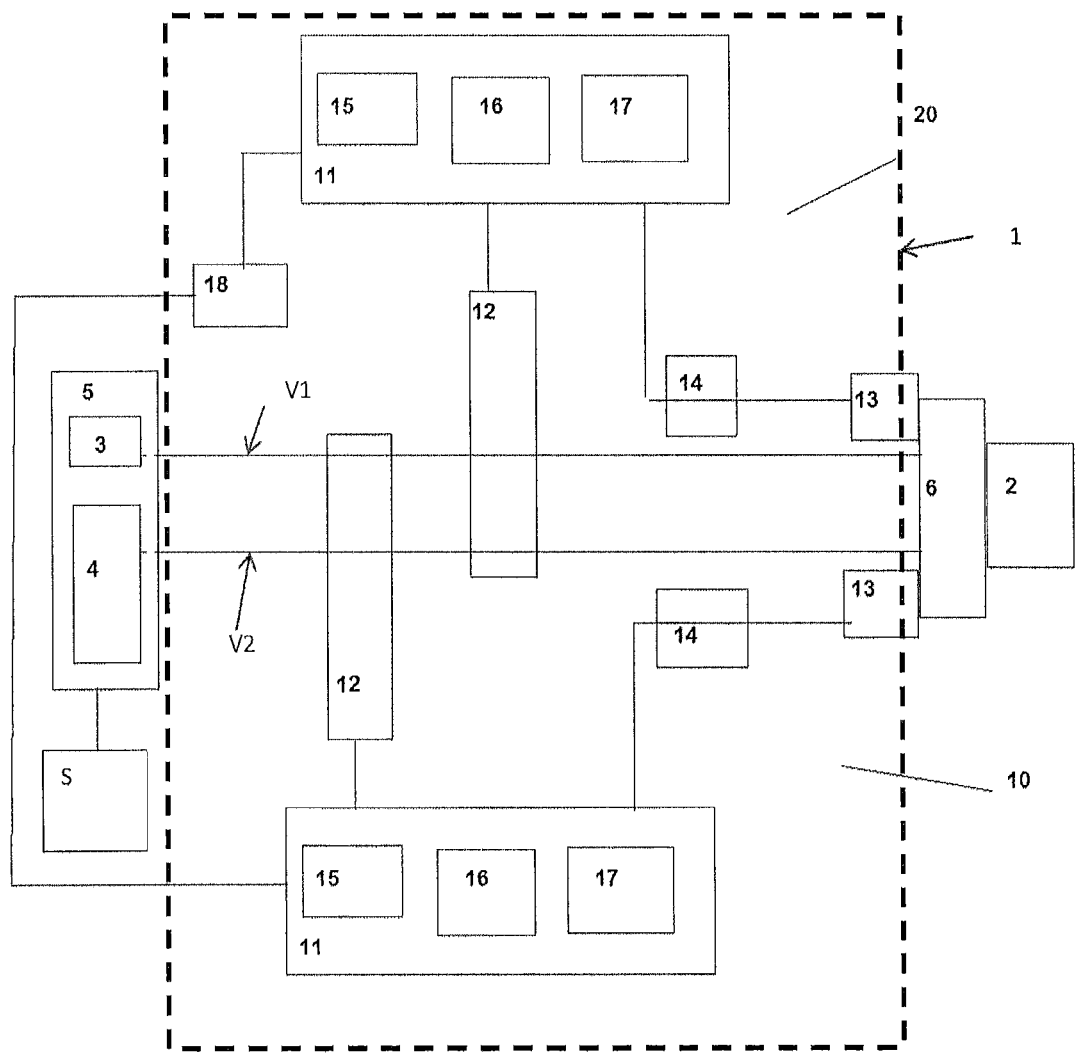
FIG. 2 illustrates, diagrammatically, a second example implementation of a device for managing the operation of an artificial heart in accordance with the invention.

In a non-restrictive implementation illustrated in FIG. 2, management device 1 can also be connected to mains power supply S; in this case the two batteries 3 and 4 are present, but the electrical energy is provided by a power supply supplied by mains power S. Batteries 3 and/or 4 are used only as back up when there is a power cut of mains power supply S. Mains power supply S can also enable the batteries to be recharged, and in particular portable battery 3.

Management device 1 illustrated in FIG. 1 and in FIG. 2 includes a first management channel 10 and a second management channel 20.

First management channel 10 includes management means 11 manufactured and arranged to supervise and control electrical power supply 5 of artificial heart 2, where electrical power supply 5 is formed by a portable electrical power supply 3 and a fixed electrical power supply 4 of a hospital console.

First management channel 10 also includes first insulation means 12, manufactured and arranged to insulate artificial heart 2 electrically from electrical power supply 5. By this means, when artificial heart 2 is connected to an electrical power supply 5, for example during the post-operative period, management device 1 then enables, for example, artificial heart 2 to be protected against an over-current. First insulation means 12 are also manufactured and arranged to insulate artificial heart 2 electrically from management means 11. For example, first insulation means 12 are compliant with standard NF-EN 60601-1.

It should be noted that portable electrical power supply 3 can be of the lithium type or the hydrogen cell type.

First management channel 10 also includes an interface 13 for communicating with artificial heart 2. This communication interface 13 can, for example, be of the CAN or RS232 type. In the case of a communication interface 13 of the RS232 type, first management channel 10 includes a communication insulator 14 installed between management means 11 and communication interface 13 of the RS232 type. In the case of a communication interface 13 of the CAN type, first management channel 10 includes a communication insulator 14 installed between management means 11 and communication interface 13 of the CAN type.

First management channel 10 also includes measuring means 15 manufactured and arranged to measure the atmospheric pressure. These measuring means 15 can be formed by a pressure sensor communicating with artificial heart 2 via communication interface 13. These measuring means 15 are also manufactured and arranged to communicate with management means 11.

First management channel 10 includes warning means 16 manufactured and arranged to communicate with management means 11 so as to create a warning. These warning means 16 can be formed by a warning light and/or by a buzzer.

Management means 11 are able, and manufactured, to detect a malfunction of electrical power supply 5, a malfunction of the communication with artificial heart 13, a malfunction of a second management channel 20 or, generally, a malfunction of artificial heart 2. Thus, when a malfunction of electrical power supply 5 occurs and is detected by management means 11 management means 11 can then alter first insulation means 12 to protect artificial heart 2. In addition, when a malfunction of artificial heart 2 is detected by management means 11 the latter can activate an alarm intended to inform a practitioner and/or the wearer of artificial heart 2.

First management means 10 also include at least one interface 17 manufactured and arranged to allow communications between management means 11 and an external device. For example, this interface 17 may be of the Ethernet, USB or Wi-Fi type, or any other interface enabling management means 11 to be connected, by wired or wireless means, with an external device.

Management device 1 also includes a second management channel 20; second management channel 20 is Identical to first management channel 10, except for interface 13 for communicating with artificial heart 2, which may be different. Consequently, in the example illustrated in FIG. 1, second management channel 20 includes:
- management means 11 manufactured and arranged to supervise and control electrical power supply 5 of artificial heart 2,
- first insulation means 12 manufactured and arranged to insulate artificial heart 2 electrically from electrical power supply 5, and from management means 11,
- an interface 13 for communicating with artificial heart 2; in the case of a communication interface 13 of the RS232 type 13 second communication channel 20 also includes a communication insulator 14 installed between management means 11 and communication interface 13 of the RS232 type; in the case of a communication interface 13 of the CAN type, second management channel 20 also includes a communication insulator 14 installed between management means 11 and communication interface 13 of the CAN type,
- measuring means 15 manufactured and arranged to measure the atmospheric pressure,
- warning means 16 manufactured and arranged to communicate with management means 11 so as to create a warning following a malfunction of electrical power supply 5, a malfunction of the communication with artificial heart 13, a malfunction of first management channel 10 and/or a malfunction of artificial heart 2,
- at least one interface 17 manufactured and arranged to allow communications between management means 11 and an external device.

It should be noted that first management channel 10 and second management channel 20 are installed in parallel. In order to protect first management channel 10 from second management channel 20, and vice versa, management device 1, which is in accordance with the invention, includes second means 18 for insulating first management channel 10 with second management channel 20.

In other words, management device 1 is formed from two management channels 10 and 20 operating completely independently from one another. Each of the two channels can in particular manage:
- the electrical energy sources, to ensure that the electrical energy is indeed supplied to artificial heart 2, in a precise manner,
- a communication link with artificial heart 2, for example a link of the CAN type to first channel 10 and a link of the RS232 type to second channel 20,
- a warning in the event of a failure of electrical power supply 5 and/or of artificial heart 2 and/or of management channels 10 and 20, by means of a sound and/or visual alarm,
- dialogue with the other management channel, so as to detect a malfunction of the other channel.

In addition, in the illustrated example, management means 11 are powered electrically via electrical power supply 5.

Figure 3:
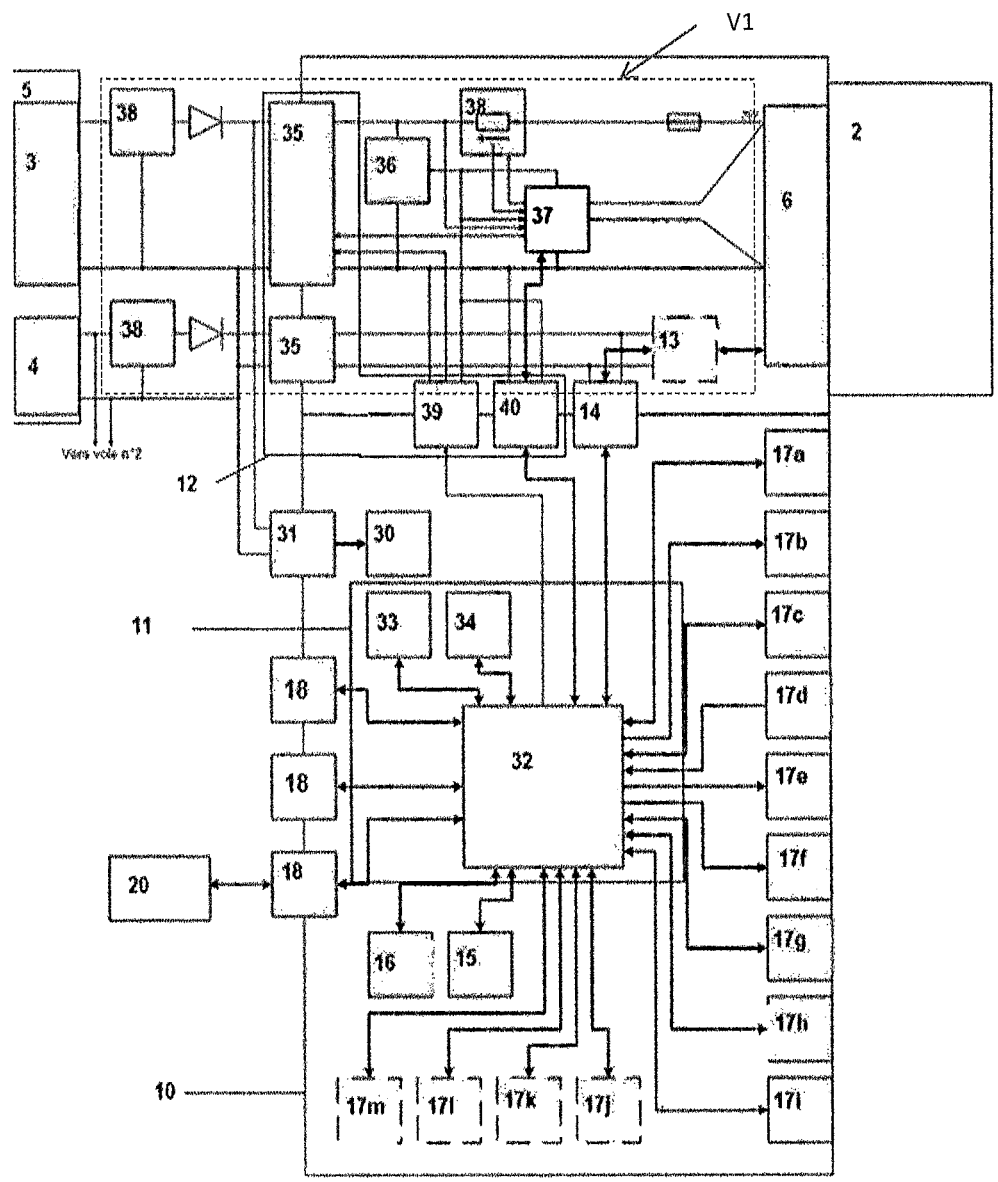
FIG. 3 illustrates, diagrammatically, a third example implementation of a device for managing the operation of an artificial heart in accordance with the invention.

FIG. 3 illustrates an example implementation of a management channel 10 of management device 1 which is in accordance with the invention. A single management channel is represented for the sake of clarity.

In this non-restrictive example, management channel 10 includes management means 11 manufactured and arranged to supervise and control electrical power supply 5 of artificial heart 2. In this example, electrical power supply 5 is formed by a portable electrical power supply 3 and a fixed electrical power supply 4. These two electrical power supplies are connected to a connection interface 6 connected to artificial heart 2 via a first electrical power supply channel V1. The layout of this electrical power supply channel V1 is given here as an example, and may be different. In addition, the various functions of the various represented models of electrical power supply channel V1 will be described below.

Electrical power supply 5 is also used to supply energy to power supply 30 supplying power to management means 11. To accomplish this a converter 31 of the DC/DC type is installed between electrical power supply 5 and power supply 30 supplying power to management means 11. The electrical power supplied to management means 11 may be of the order of 5 V. DC/DC type converter 31 may be compliant with standard NF-EN 60601-1.

As an illustration, management means 11 can be formed by:
- a processor 32, for example of the I.MX6 type,
- a dynamic memory 33, where this dynamic memory can, for example, be formed by four units of the DDR3L type of 256 MB to 1 GB each, and
- a mass storage device 34, for example of the eMMC type, of 8 GB to 64 GB.

This implementation means that a high degree of functionality can be accomplished with a minimum of components. Due to this feature, each of management means 11 consumes less than 5 W. As a consequence, most of electrical power supply 5 is supplied to artificial heart 2.

Management channel 10 includes not only management means 11 manufactured and arranged to supervise and control electrical power supply 5 of artificial heart 2, but also first insulation means 12 manufactured and arranged to insulate artificial heart 2 electrically from management means 11, where these management means 11 can be connected to a fixed potential via one or more external connections. First insulation means 12 are also manufactured and arranged to insulate artificial heart 2 electrically from electrical power supply 5.

In general terms, management means 11 and first insulation means 12 communicate in order to be able:
- to halt to the operation of insulated DC/DC converter units 35; this function may be used for self-test requirements, or for safety problems (e.g.: when management means 11 detect that artificial heart 2 has been short-circuited for a determined period); these insulated DC/DC converter units 35 enable artificial heart 2 to be insulated electrically from electrical supply 5, if necessary,
- to supervise the power voltages to detect faults of artificial heart 2,
- to adjust the voltage, via isolated DC/DC converter units 35 controlled by controller 37, powered by voltage regulator 36, to allow a balancing of the current supplied by each electrical power supply channel,
- to measure the current, via controller 37, supplied to artificial heart 2 (this information enables a confirmation to be obtained that the power is indeed being supplied to artificial heart 2), in order to detect, via controller 37, over-currents in the current supplied to artificial heart 2, or to run tests of protective units 38 against excess voltage or over-currents; these tests may consist, for example, in lowering the detection threshold in order to check that it is activated.

All communications between management means 11 and the functions powering artificial heart 2 are made through first insulation means 12, and comply, for example, with standard NF-EN 60601-1, with leakage currents below category CF (leakage currents of 0.22 µA typically with 264 V 60 Hz per insulator).

These first insulation means 12 can include not only insulated DC/DC converter units 35, but also a digital insulator 39 and an insulator of the I2C type 40.

Insulated DC/DC converter units 35 in particular enable artificial heart 2 to be insulated electrically from electrical power supply 5.

Digital insulator 39 and insulator of the I2C type 40 in particular enable artificial heart 2 to be insulated electrically from management means 11.

In addition, management channel 10 includes an interface 13 for communicating with artificial heart 2. This communication interface 13 can be of the CAN or RS232 type. In the case of a communication interface 13 of the RS232 type, a communication insulator 14 is installed between management means 11 and communication interface 13 of the RS232 type.

In general terms, communication between management means 11 and artificial heart 2 can be made:
over a management channel (for example, first management channel 10), via a communication interface of the RS232 type, after passing through a communication insulator 14, and upgrading by an RS232 driver 13,
over the other management channel (second management channel 20), via a communication interface of the CAN type through a communication insulator, without requiring any CAN driver.

It will be understood that first management channel 10 may include a communication interface 13 of the CAN or RS232 type, and second management channel 20 may include a communication interface 13 of the CAN or RS232 type.

In addition, management channel 10 includes measuring means manufactured and arranged to measure atmospheric pressure 15. These means for measuring atmospheric pressure 15 may be formed by a pressure sensor. The sensor may also be welded on to the electronic card of processor 32 included in management means 11.

Management channel 10 also includes warning means 16 manufactured and arranged to communicate with management means 11. These warning means 16 enable the wearer of artificial heart 2 and/or a hospital to be warned if an operating fault of electrical power supply 5 and/or of artificial heart 2 and/or of management channels 10 and 20 is detected by management means 11. These warning means 16 can, for example, be formed by a buzzer communicating with management means 11.

In addition, management channel 10 includes external interfaces manufactured and arranged to allow communications between management means 11 and internal and/or external devices.

In the illustrated example external interfaces 17 are formed by:
An interface of the RS232 type 17a, for example allowing a pressure sensor to be connected,
A video interface 17b of the LVDS or RGB parallel type enabling a screen included in management means 11 to be connected,
A first interface 17c of the USB 2 or SPI type enabling a touchscreen included in management means 11 to be connected,
A matrix keyboard interface 17d enabling a keyboard included in management means 11 to be connected,
An interface 17e enabling warning lights which may be used to generate an alert to be connected;
A video interface of the HDMI type 17f enabling an external screen to be connected,
A second interface 17g of the USB 2 type enabling an external touchscreen to be connected,
A third interface 17h of the USB 2 type enabling an external connection to be connected,
A Gigabit Ethernet interface 17i enabling an external device to be connected,
An interface 17j enabling a disk of the SSD type to be connected, where this disk of the SSD type can be embedded by management means 11, or be external to them,
An interface 17k enabling a modem of the Wi-Fi type to be connected,
An interface 17l enabling a modem of the Bluetooth type to be connected,
An interface 17m enabling a modem of the GSM type to be connected.

It should be noted that these interfaces 17 are listed as indications only. Those skilled in the art will be able to remove certain these or add others, without however going beyond the scope of the invention.

In addition, management device 1 for managing the operation of an artificial heart according to the invention includes a second management channel 20. This second management channel 20 is identical to first management channel 10. First management channel 10 and second management channel 20 are installed in parallel. These two management channels 10 and 20 are insulated from one another via second insulation means 18. These second insulation means 18 can be formed by an isolator of a digital type. More specifically, second insulation means 18 can be formed by I2C isolators (SMBus compatible). These insulation means 18 enable a dialogue to be established with electrical power supply 5 in order to obtain, in particular:
The voltage,
The transmitted current,
The battery's remaining capacity,
The battery's temperature,
The battery's condition.

This information is essential for the patient's safety when management device 1 is in autonomous mode. In addition, these second insulation means 18 ensure complete independence of the two management channels even in the event of a fault in one of the two management channels.

What is claimed is:

1. A device for managing operation of an artificial heart, said device for managing the operation of the artificial heart comprising a first management channel, a second management channel, wherein said first management channel and said second management channel are installed in parallel and each include:
an electrical power supply formed by a portable electrical power supply and a fixed electrical power supply,
a management system constructed and arranged to supervise and control the electrical power supply of the artificial heart, the management system including a microprocessor and one or more memories connected to the microprocessor, and a first insulation system including one or more DC/DC converter units constructed and arranged to insulate the artificial heart electrically from the electrical power supply, and from the management system, the microprocessor being connected to the first insulation system to adjust, via the one or more DC/DC converter units, a voltage supplied by the electrical power supply, wherein said device for managing the operation of the artificial heart further comprises a second insulation system that includes one or more I2C isolators constructed and arranged to insulate the first management channel from the second management channel such that the first management channel and the second management channel are configured to be operated by the device for managing the operation of the artificial heart completely independently from one another.

2. The device for managing the operation of an artificial heart according to claim 1, wherein the first insulation system is in compliance with standard NF-EN 60601-1.

3. The device for managing the operation of an artificial heart according to claim 1, wherein the first management channel also includes an interface for communicating with the artificial heart, formed by the interface of a CAN or RS232 type.

4. The device for managing the operation of an artificial heart according to claim 1, wherein the first management channel includes a pressure sensor constructed and arranged to measure atmospheric pressure.

5. The device for managing the operation of an artificial heart according to claim 1, wherein the first management channel includes a warning light or a buzzer to warn a user when an operational fault of the electrical power supply, of the first management channel, of the second management channel and/or of the artificial heart is detected by the management system.

6. The device for managing the operation of an artificial heart according to claim 1, wherein the first management channel includes at least one external interface constructed and arranged to allow communications between the management system and an external device.

* * * * *